(12) United States Patent
Takahashi et al.

(10) Patent No.: US 8,080,202 B2
(45) Date of Patent: Dec. 20, 2011

(54) COMPONENT SEPARATING DEVICE AND CHEMICAL ANALYSIS DEVICE USING THE SAME

(75) Inventors: Makoto Takahashi, Osaka (JP); Masaya Nakatani, Hyogo (JP)

(73) Assignee: Panasonic Corporation, Osaka (JP)

( * ) Notice: Subject to any disclaimer, the term of this patent is extended or adjusted under 35 U.S.C. 154(b) by 448 days.

(21) Appl. No.: 12/444,485

(22) PCT Filed: Nov. 15, 2007

(86) PCT No.: PCT/JP2007/072173
§ 371 (c)(1), (2), (4) Date: Apr. 6, 2009

(87) PCT Pub. No.: WO2008/065897
PCT Pub. Date: Jun. 5, 2008

(65) Prior Publication Data
US 2010/0078323 A1    Apr. 1, 2010

(30) Foreign Application Priority Data
Nov. 27, 2006 (JP) .................................. 2006-318239

(51) Int. Cl.
*B01D 43/00* (2006.01)
(52) U.S. Cl. ............ 422/20; 422/22; 422/502; 422/503; 422/504; 422/518; 422/527; 366/108; 366/114; 366/127; 210/748.01; 210/748.02; 210/748.05
(58) Field of Classification Search .................... 422/20, 422/22, 502–504, 518, 527; 366/108, 111, 366/114, 127, 174.1; 210/748.01, 748.02, 210/748.05
See application file for complete search history.

(56) References Cited

U.S. PATENT DOCUMENTS

| 6,432,630 | B1 | 8/2002 | Blankenstein |
| 7,871,827 | B2* | 1/2011 | Parthasarathy et al. ........ 436/180 |
| 7,927,865 | B2* | 4/2011 | Meathrel et al. ............ 435/287.2 |
| 7,968,049 | B2* | 6/2011 | Takahashi et al. .............. 422/20 |
| 2002/0106314 | A1* | 8/2002 | Pelrine et al. .................. 422/186 |

(Continued)

FOREIGN PATENT DOCUMENTS
JP    2002-503334 A    1/2002
(Continued)

OTHER PUBLICATIONS

International Search Report for PCT/JP2007/072173, filed Feb. 19, 2008.

(Continued)

*Primary Examiner* — Brian R Gordon
(74) *Attorney, Agent, or Firm* — RatnerPrestia

(57) ABSTRACT

A vibrator has a large strength of a standing wave even with a low driving voltage, thereby improving the accuracy of component separation. A device according to the present invention includes a substrate having a channel groove provided in an upper surface of the substrate, a seal provided above the substrate so as to cover an upper opening of the channel groove, a projection provided on an outer side wall opposite to the channel groove, and a vibrator causing the projection to warp and vibrate in a depth direction of the channel groove. The warping vibration of the projection is amplified due to effect of leverage, and generates a large stress on the outer wall of the channel groove having the projection provided thereon. Consequently, the strength of a standing wave in the channel groove increases even for a low driving voltage, thereby improving the accuracy of component separation.

13 Claims, 10 Drawing Sheets

U.S. PATENT DOCUMENTS

| | | | |
|---|---|---|---|
| 2003/0027354 A1* | 2/2003 | Geli | 436/178 |
| 2003/0138819 A1* | 7/2003 | Gong et al. | 435/6 |
| 2003/0175947 A1* | 9/2003 | Liu et al. | 435/288.5 |
| 2004/0069717 A1 | 4/2004 | Laurell et al. | |
| 2004/0257906 A1* | 12/2004 | Scriba et al. | 366/127 |
| 2007/0287185 A1* | 12/2007 | Vafai et al. | 436/63 |
| 2008/0103297 A1* | 5/2008 | Parthasarathy et al. | 536/25.4 |
| 2009/0250406 A1 | 10/2009 | Takahashi et al. | |
| 2010/0068824 A1* | 3/2010 | Kimura | 436/501 |
| 2010/0098585 A1* | 4/2010 | Chiu et al. | 422/68.1 |
| 2010/0126922 A1* | 5/2010 | Takahashi et al. | 210/201 |

FOREIGN PATENT DOCUMENTS

| | | |
|---|---|---|
| JP | 2004-535912 A | 12/2004 |
| JP | 2006-318239 | 8/2011 |
| WO | WO 2006/032048 A2 | 3/2006 |
| WO | WO 2006/032703 A1 | 3/2006 |
| WO | WO 2006/115241 A1 | 11/2006 |

OTHER PUBLICATIONS

Carl Siversson et al., "Acoustic Particle Sizing in Microchannels by Means of Ultrasonic Frequency Switching", Micro Total Analysis Systems 2004, pp. 330-332, vol. 2, 8th International Conference on Miniaturized Systems for Chemistry and Life Sciences, Sep. 26-30, 2004, Malmo, Sweden.

Holden Li et al., "Study of High Speed Acoustic Separation in Micro-Channels Using μ-PIV", Micro Total Analysis Systems 2004, pp. 12-14, vol. 1, 8th International Conference on Miniaturized Systems for Chemistry and Life Sciences, Sep. 26-30, 2004, Malmo, Sweden.

* cited by examiner

COMPONENT SEPARATING DEVICE AND CHEMICAL ANALYSIS DEVICE USING THE SAME

This application is a U.S. National Phase Application of PCT International Application PCT/JP2007/072173.

TECHNICAL FIELD

The present invention relates to a small component separating device for separating a liquid, such as blood or emulsion, into a liquid component and a solid component, and to a chemical analysis device chemically analyzing a test substance using the device.

BACKGROUND ART

A micro total analysis system which has been paid attention for as a next-generation analysis technique refers to a micrometer-scale, chemical analysis device integrating processes for introducing a test substance, i.e., a mixture of liquid and solid components, such as blood, for transferring the substance to a component separating device to separate the liquid into the components, for causing the components react with reagents, and for analyzing the reaction.

FIG. 18 is a sectional view of a conventional component separating device. As shown in FIG. 18, conventional component separating device 1 includes substrate 2, seal 3 covering above substrate 2, and vibrator 4 provided on a side of substrate 2. Substrate 2 has channel groove 5 therein for transferring a test substance. Vibrator 4 including a piezoelectric element generates an acoustic wave with a predetermined frequency. Vibrator 4 causes a solid component to concentrate at a node of an acoustic standing wave generated in channel groove 5 to separate various components. Such separation methods using acoustic waves are described in Non-patent Documents 1 and 2.

However, in conventional component separating device 1 described above, vibrator 4 requires a high driving voltage. This is because vibration from vibrator 4 diffuses to entire substrate 2 and seal 3 to attenuate the standing wave generated in channel groove 5, accordingly preventing the component from being separated accurately.

Non-patent Document 1: Carl Siversson, Micro Total Analysis Systems 2004, pp 330-332, vol. 2
Non-patent Document 2: Holden Li, Micro Total Analysis Systems 2004, pp 12-14, vol. 1

SUMMARY OF THE INVENTION

According to the present invention, the strength of a standing wave is increased even with a low driving voltage to vibrator 4. A component separating device according to the present invention includes a projection provided on an outer side wall opposite to a channel groove. A vibrator provides this projection with warping vibration in a depth direction of the channel groove. This component separating device increases the strength of a standing wave even with a low driving voltage applied to the vibrator. The warping vibration of the projection is amplified due to an effect of leverage, thereby generating a large stress at the outer side wall of the channel groove having the projection thereon. Thus, the device increases the strength of the standing wave inside the channel groove even with the low driving voltage, thereby separating the component accurately.

REFERENCE NUMERALS

6 Component Separating Device
7 Channel Groove
7a, 7b Outer Side Wall
8 Substrate
9 Seal
10, 10a to 10e Projection
11, 11a to 11e Vibrator
12 First Electrode
13 Piezoelectric Body
14 Second Electrode
15 Liquid Component
16, 16a, 16b Solid Component
17 Standing Wave
18 Node
19a Warping Vibration
19b Acoustic Wave Vibration
20a, 20b Flow
21 Chemical Analysis Device
22 Test Substance Inlet
23 Transfer Section
24 Reaction Section
25 Analysis Section
26 Silicon Substrate
27 Space

DETAILED DESCRIPTION OF PREFERRED EMBODIMENTS

Exemplary Embodiment 1

Figure 1:
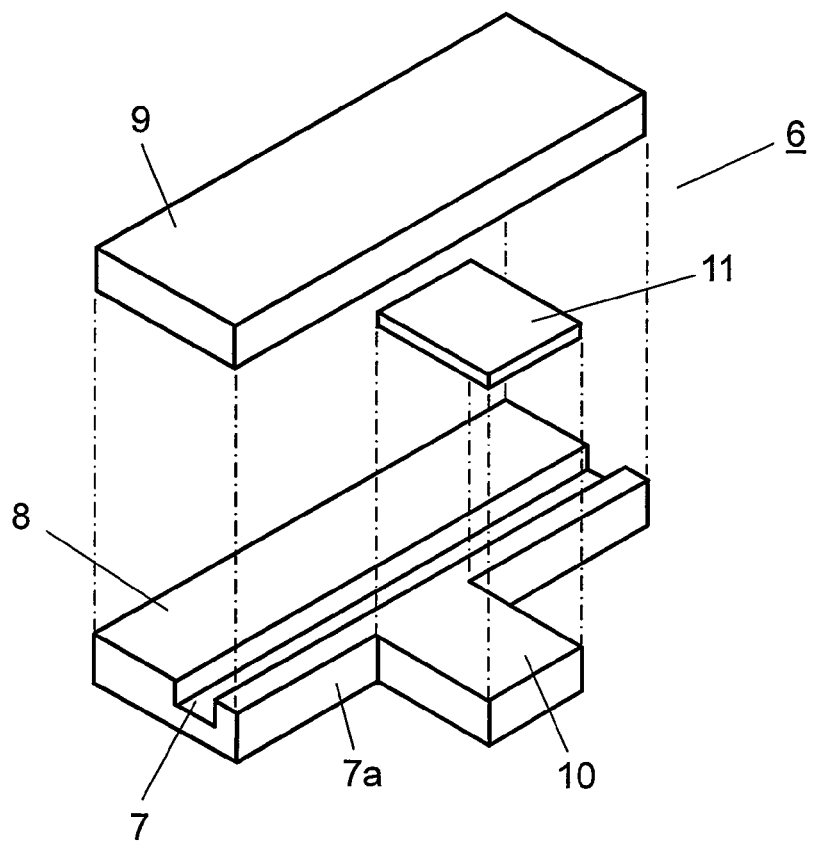
FIG. 1 is an exploded perspective view of a component separating device according to the present invention.

Component separating device 6 according to Exemplary Embodiment 1 of the present invention will be described below. FIG. 1 shows an exploded perspective view of component separating device 6 according to the embodiment. Component separating device 6 according to the embodiment shown in FIG. 1 includes substrate 8 having channel groove 7 opening in a upper surface of the substrate, seal 9 provided above substrate 8 so as to cover the opening of channel groove 7, projection 10 provided on outer side wall 7a of the substrate opposite to channel groove 7, and vibrator 11 provided on an upper surface of projection 10. Substrate 8 and seal 9 are joined together with an adhesive. According to this embodiment, substrate 8 and seal 9 are made of silicon and glass, respectively. Seal 9 may be made of plastic or silicon besides glass.

Figure 2:
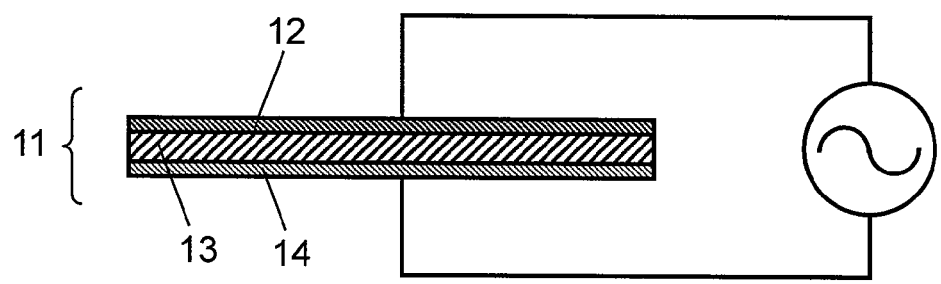
FIG. 2 is a sectional schematic view of a vibrator according to the invention.

FIG. 2 is a schematic sectional view of vibrator 11. As shown in FIG. 2, vibrator 11 includes first electrode 12 made of titanium or platinum, piezoelectric body 13 made of lead zirconate titanate, and second electrode 14 made of titanium or gold in the order from projection 10 (shown in FIG. 1). An alternating-current (AC) voltage is applied between first electrode 12 and second electrode 14 to cause projection 10 to warping and vibrating in a depth direction of channel groove 7. The vibrator made of these materials converts electric energy to mechanical energy efficiently, thereby being displaced even if with the voltage driving the vibrator is low.

Figure 3:
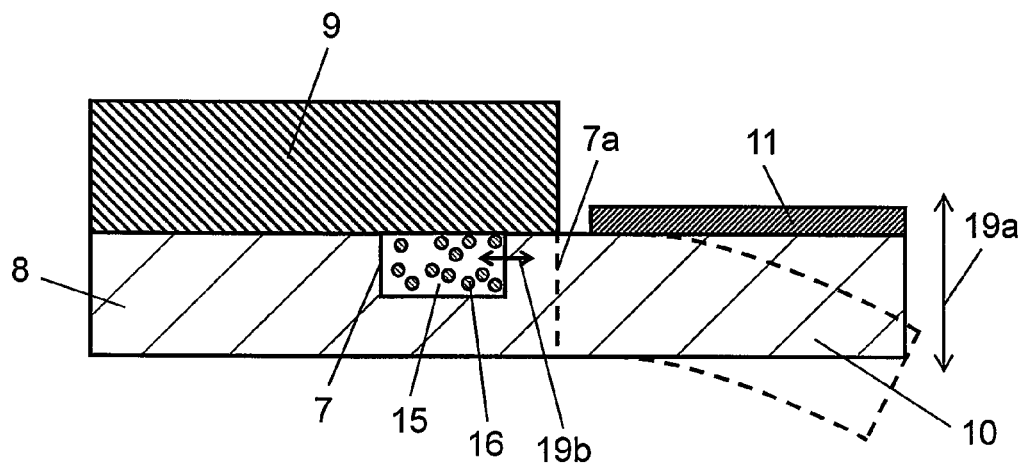
FIG. 3 is a schematic sectional view of the component separating device according to the invention for illustrating an operation of the device.
Figure 4:
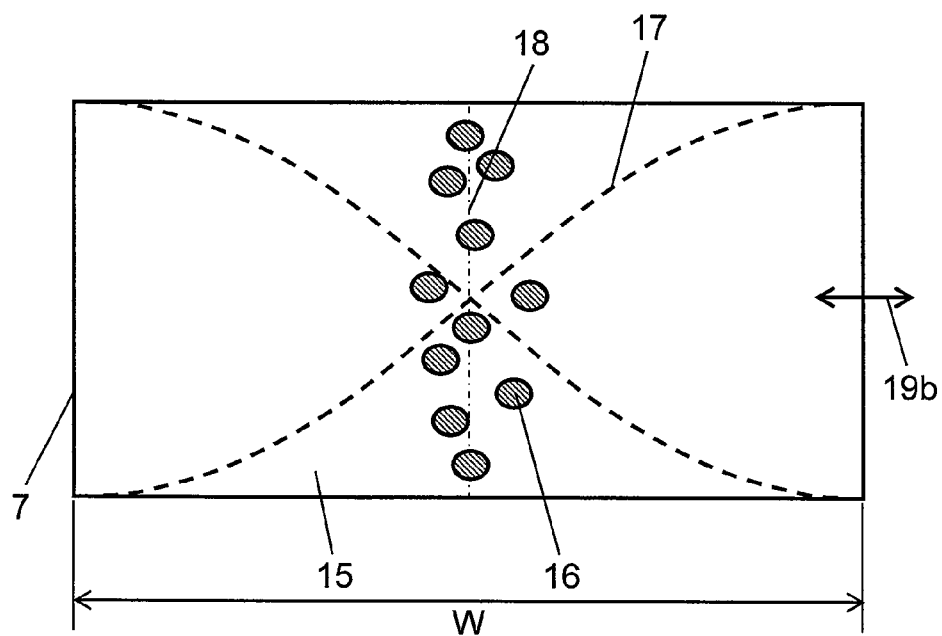
FIG. 4 is a schematic sectional view of a channel groove according to the invention.

FIG. 3 is a schematic sectional view of component separating device 6 for illustrating an operation of the device. As shown in FIG. 3, channel groove 7 has a predetermined width and a predetermined depth so as to contain a mixture of liquid component 15 and solid component 16 therein and to allow the mixture through the groove. The width of channel groove 7 is determined to generate a predetermined standing wave in channel groove 7. FIG. 4 shows the channel groove. Standing wave 17 is represented by the dotted lines in FIG. 4.

A method of designing channel groove 7 will be described below with reference to FIG. 4. Channel groove 7 has width W. A speed of sound in liquid component 15 out of a mixture of liquid component 15 and solid component 16 introduced to channel groove 7 is v. An acoustic wave with frequency f satisfying:

$$f = (n/2) \times v/W \text{ (where } n \text{ is a natural number)}$$

is applied to channel groove 7 to generate standing wave 17 in channel groove 7.

According to this embodiment, projection 10 has a shape having frequency f as its primary resonance frequency.

Substrate 8 and projection 10 are made of a single substrate. This structure maintains the strength of substrate 8 and projection 10 even if a portion at which substrate 8 is connected with projection 10 has a stress due to warping vibration 19a of projection 10. In FIG. 3 arrow 19a represents the direction of warping vibration 19a.

An operation of component separating device 6 according to the embodiment will be described below. First, as shown in FIG. 3, a mixture of liquid component 15 and solid component 16 is introduced into channel groove 7. When a driving voltage providing vibration with frequency f is applied to vibrator 11, projection 10 warps and vibrates as warping vibration 19a so as to have its shape change as shown by the dotted lines in FIG. 3 in response to this driving voltage. Projection 10 is shorter than substrate 8 in a longitudinal direction of the substrate, hence allowing projection 10 to deform and vibrate easily. Since outer side wall 7a opposite to channel groove 7 is connected with projection 10, vibration caused by warping vibration 19a of projection 10 propagates, as an acoustic wave, to outer side wall 7a of channel groove 7. Arrow 19b in FIG. 3 represents the vibration due to this acoustic wave. According to this embodiment, projection 10 and outer side wall 7a are made of a single substrate, and allows the acoustic wave to efficiently propagate with a low propagation resistance. Then, this acoustic wave generates standing wave 17 in channel groove 7, as shown in FIG. 4. Standing wave 17 applies a force to solid component 16 in a direction toward node 18 of standing wave 17, thereby allowing solid component 16 to concentrate to node 18.

Figure 5:
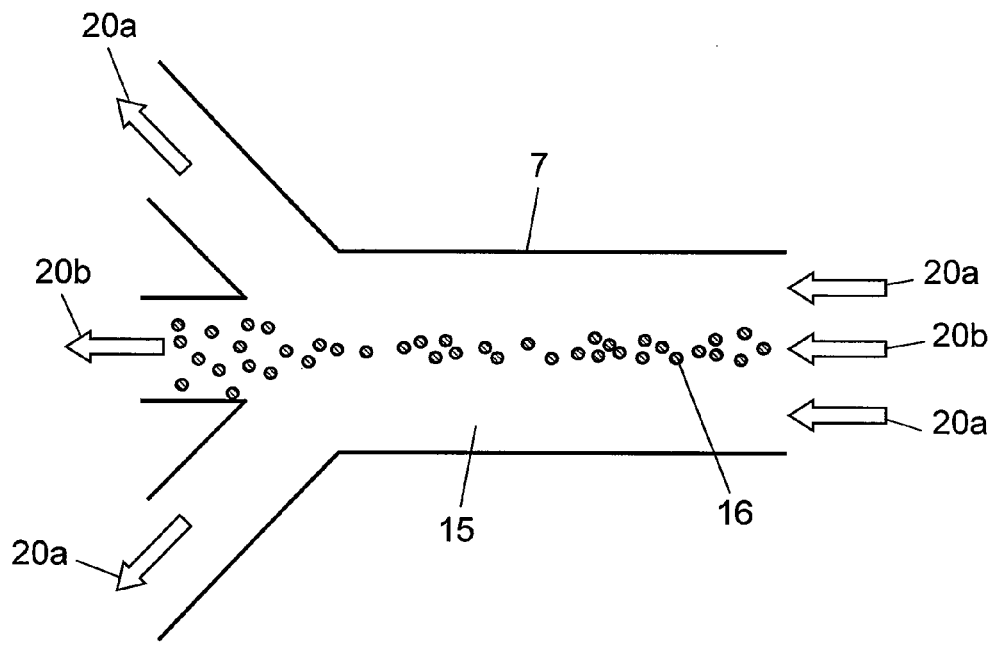
FIG. 5 is a schematic top view of the channel groove according to the invention.

FIG. 5 is a schematic top view of a channel according to the invention. As shown in a top view of channel groove 7 in FIG. 5, the mixture is separated into liquid component 15 and solid component 16 in channel groove 7, and then flow 20a mainly containing liquid component 15 and flow 20b of solid component 16 highly concentrating are divided at a branch of channel groove 7, thus extracting component 15 and solid component 16 separately.

Projection 10 has a primary resonance frequency equal to frequency f, hence producing warping vibration 19a with a large displacement more efficiently than a projection having other shapes. This structure provides standing wave 17 with a large strength, providing component separating device 6 with a small size.

Figure 18:
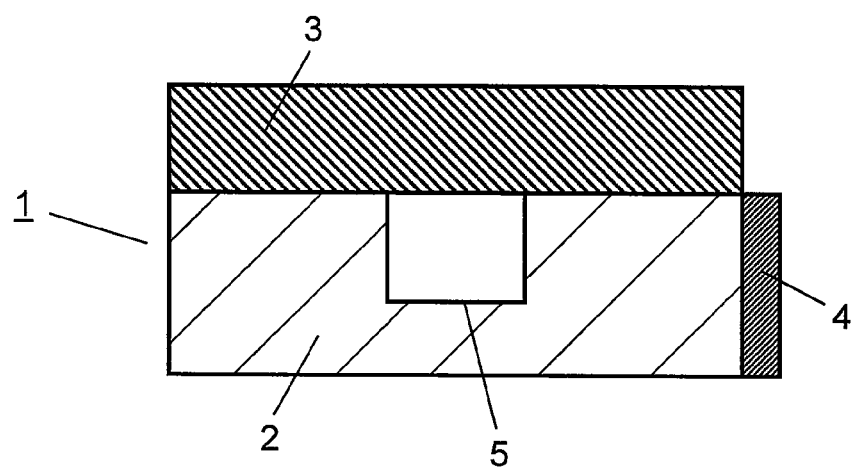
FIG. 18 is a sectional view of a conventional component separating device.

Effects according to the embodiment will be described below. Component separating device 6 according to this embodiment can increase the strength of standing wave 17 even with a low driving voltage to vibrator 11. More specifically, in conventional component separating device 1, vibrator 4 is directly stuck on the side of substrate 2, as shown in FIG. 18. According to this embodiment, on the other hand, channel groove 7 has projection 10 on outer side wall 7a opposite to channel groove 7, as shown in FIG. 3. Projection 10 has vibrator 11 thereon. According to this embodiment, warping vibration 19a of projection 10 propagates as an acoustic wave intensively to outer side wall 7a opposite to channel groove 7 having projection 10 provided thereon. At this moment, the vibration is amplified due to effect of leverage, thereby producing a large stress at outer side wall 7a opposite to channel groove 7, which is a supporting point and a working point of the leverage. Consequently, the strength of standing wave 17 in channel groove 7 increases even for a low driving voltage and for a small vibrator 11, thereby improving the component-separation accuracy. The vibration propagates to entire substrate 8 and seal 9, and attenuates. However, according to this embodiment, the strength of standing wave 17 is previously increased, accordingly preventing separation accuracy from deteriorating.

The width and arrangement of projections 10 may be appropriately adjusted to generate standing wave 17 at a predetermined position of channel groove 7, thereby improving the accuracy of component separation.

Vibrator 11 according to this embodiment having a laminated structure with superior adhesion maintains high durability even against repetitive displacement. Vibrator 11 according to this embodiment made of the aforementioned materials can be pattern-molded accurately by, e.g. dry etching on projection 10 after sputtering. This process forms vibrator 11 accurately at a desired portion of channel groove 7 where standing wave 17 is generated.

Figure 6:
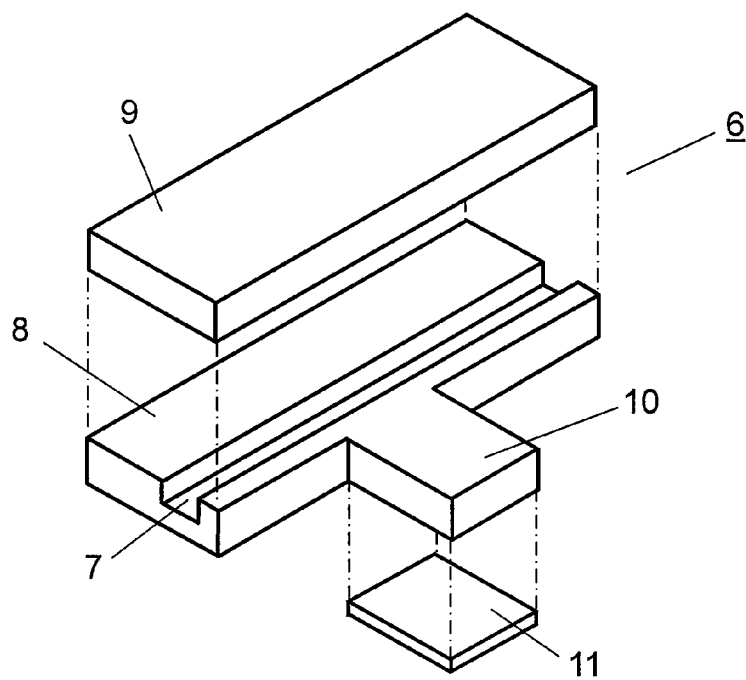
FIG. 6 is an exploded perspective view of the component separating device according to the invention.

FIG. 6 is an exploded perspective view of another component separating device 6 according to the present invention. In the above mentioned device, vibrator 11 is provided on the upper surface of projection 10. As shown in FIG. 6, vibrator 11 may be provided on a lower surface of the projection. Vibrator 11 provided on the lower surface can be wired arbitrarily without interfering with channel groove 7 and seal 9.

Exemplary Embodiment 2

Figure 7:
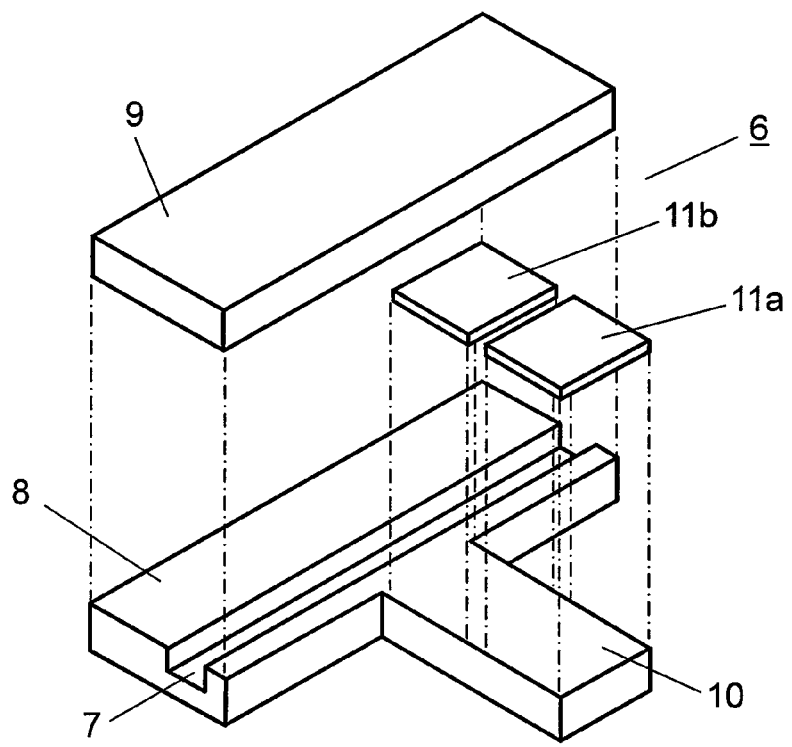
FIG. 7 is an exploded perspective view of the component separating device according to the invention.
Figure 8:
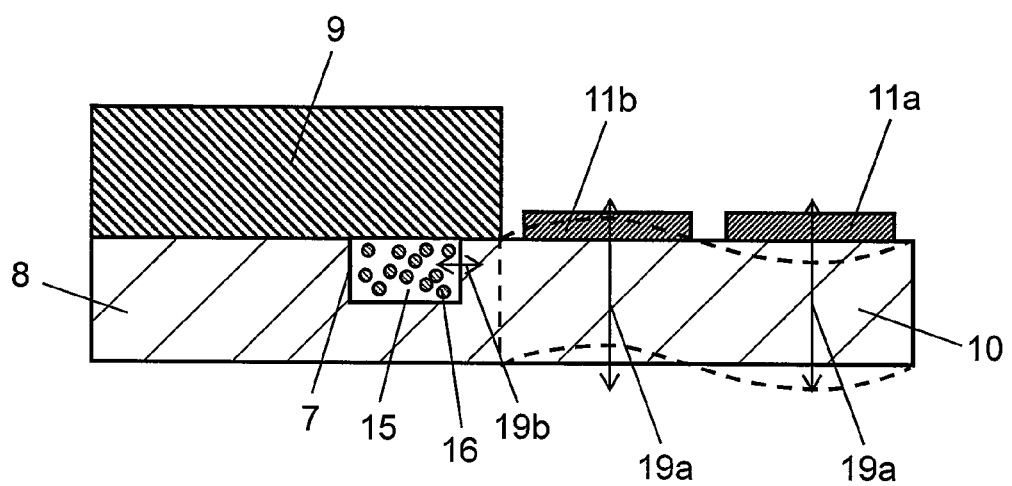
FIG. 8 is a schematic sectional view of the component separating device according to the invention for illustrating an operation of the device.

FIG. 7 is an exploded perspective view of component separating device 6 according to Exemplary Embodiment 2 of the present invention. The device according to Embodiment 2 is different from the device according to Embodiment 1 in that two vibrators 11a and 11b having shapes identical to each other are provided on the upper surface of projection 10, as shown in FIG. 7, and that the shape of projection 10 is designed so that frequency f is a secondary resonance frequency of the projection. FIG. 8 schematically shows the relationship between the shape of projection 10 and the resonance frequency represented by curved dotted lines.

According to this embodiment, this structure increases the strength of standing wave 17 generated in channel groove 7, thereby improving the separation accuracy of component separating device 6. In the case that frequency f is extremely high, only one small vibrator 11 can be provided on the projection to use a primary resonance of the warping vibration of projection 10, hence causing generating weak standing wave 17. If only one large vibrator is provided to use higher-order resonance, the resonance is not produced efficiently since the piezoelectric body can hardly deform. According to this embodiment, plural vibrators 11 arranged on projection 10 produce higher-order resonance at projection 10 efficiently, thus generating standing wave 17 with sufficient strength.

For example, according to this embodiment, driving voltages having frequency f and having phases different from each other by 180 degrees are applied to vibrators 11a and 11b, respectively, as shown in FIG. 8, thereby producing warping vibration 19a of the secondary resonance efficiently. Consequently, the mixture of liquid component 15 and solid component 16 can be separated and extracted efficiently into liquid component 15 and solid component 16 even for extremely high frequency f similarly to the device according to Embodiment 1. The number of vibrators 11 may be changed to adjust the strength of standing wave 17 over a wide range.

Exemplary Embodiment 3

Figure 9:
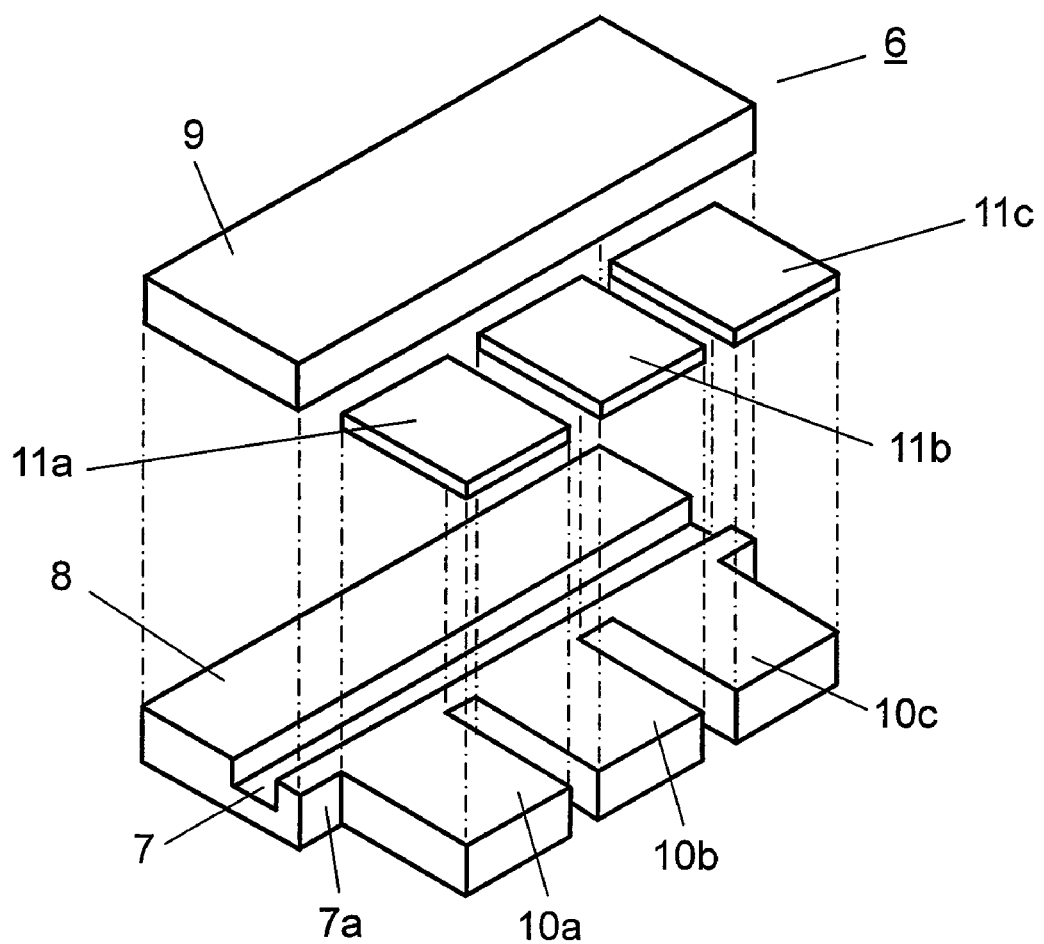
FIG. 9 is an exploded perspective view of the component separating device according to the invention.

FIG. 9 is an exploded perspective view of component separating device 6 according to Exemplary Embodiment 3 of the present invention. The device according to Embodiment 3 is different from the device according to Embodiment 1 in that plural projections 10a to 10c having shapes identical to each other are provided on outer side wall 7a of one side of the substrate opposite to channel groove 7, and that vibrators 11a to 11c are provided on upper surfaces of projections 10a to 10c, respectively, as shown in FIG. 9. This structure generates standing wave 17 in a large area, accordingly causing solid component 16 to concentrate sufficiently even if solid component 16 is too small to receive a large force due to a sound pressure of the standing wave for concentrating. Further, this device can suppress side-effect vibrations more than a device including projection 10 having an elongated side parallel to channel groove 7, accordingly enabling more efficient component separation.

Figure 10:
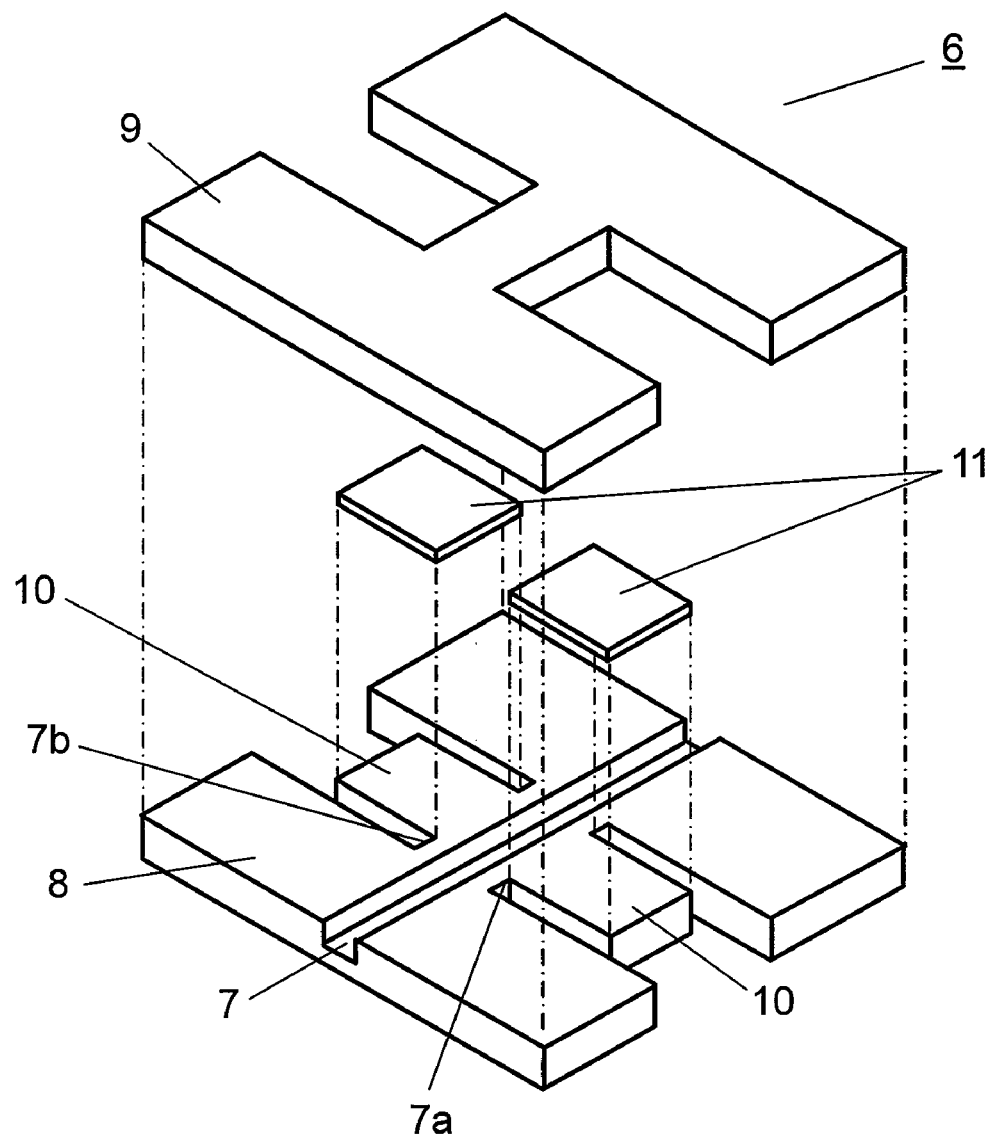
FIG. 10 is an exploded perspective view of the component separating device according to the invention.

FIG. 10 is an exploded perspective view of component separating device 6 having another shape. In FIG. 9, projections 10 are provided on outer side wall 7a at one side opposite to channel groove 7. In FIG. 10, projections 10 are provided on outer side walls 7a and 7b at both sides of the substrate opposite to channel groove 7. In this case, acoustic waves propagating from both sides of channel groove 7 generates standing wave 17 with large strength.

Exemplary Embodiment 4

Figure 11:
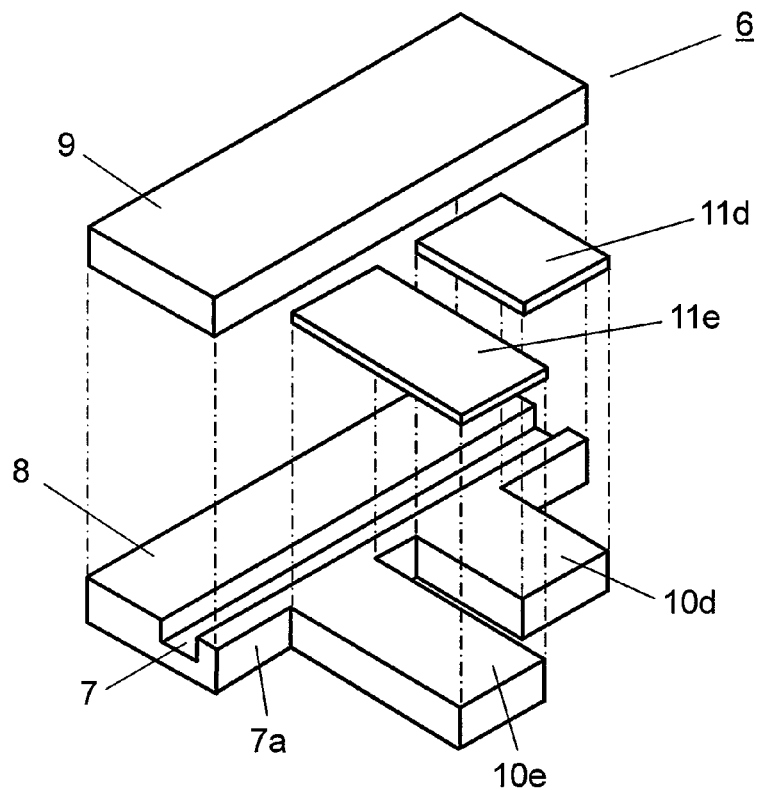
FIG. 11 is an exploded perspective view of the component separating device according to the invention.

FIG. 11 is an exploded perspective view of component separating device 6 according to Exemplary Embodiment 4. The device according to Embodiment 4 is different from the device according to Embodiment 1 in that two projections 10d and 10e having shapes different from each other are provided on outer side wall 7a of the substrate opposite to channel groove 7, as shown in FIG. 11.

Figure 12:
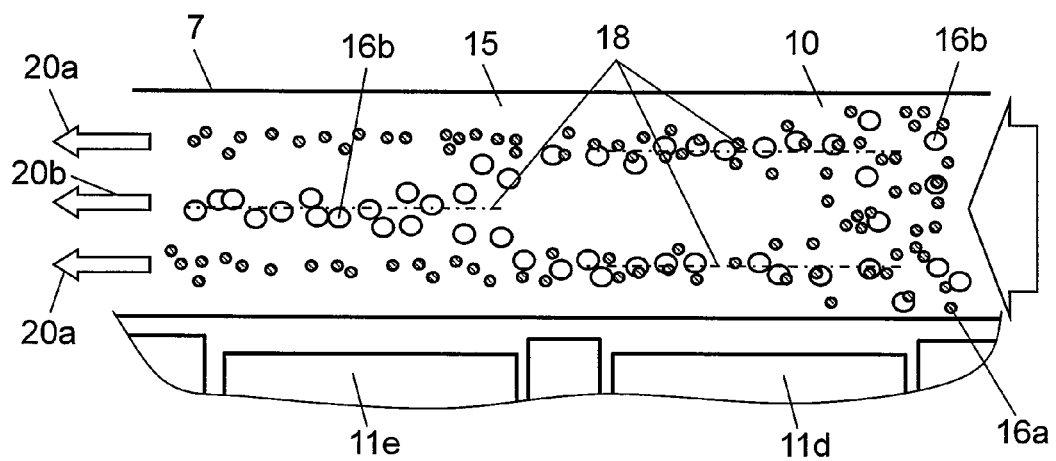
FIG. 12 is a schematic top view of the component separating device according to the invention.

FIG. 12 is a schematic top view of channel groove 7. Small solid component 16a and large solid component 16b are mixed with liquid component 15. According to this embodiment, the shape of first projection 10d is determined so that frequency f1 satisfying $$f1 = n \times v/W \text{ ($n$ is a natural number)}$$

is a resonance frequency of warping vibration 19a, where W is the width of groove 7, and v is a speed of sound in liquid component 15 out of the mixture of liquid component 15 and solid components 16a and 16b introduced to channel groove 7.

The shape of second projection 10e is determined so that frequency f2 satisfying:

$$f2 = (½) \times v/W; \text{ or}$$

$$f2 = (½+n) \times v/W \text{ ($n$ is a natural number)}$$

is the resonance frequency of warping vibration 19a. Vibrators 11d and 11e are formed on the upper surfaces of projections 10d and 10e, respectively.

In the above-described structure, standing waves 17 with nodes 18 of which numbers are different from each other are generated, as shown in FIG. 12, thereby separating solid components 16 with different properties from each other.

A separation using component separating device 6 according to this embodiment will be described below. First, as shown in the top view of channel groove 7 of FIG. 12, the mixture of liquid component 15, small solid component 16a, and large solid component 16b is introduced to channel groove 7. When a driving voltage with frequency f3 satisfying $$f3 = v/W$$

is applied to vibrator 11d, two nodes 18 of standing wave 17 are generated in an area of channel groove 7 facing vibrator 11d. In this case, if the driving voltage is increased, both small solid component 16a and large solid component 16b sufficiently concentrate.

When a driving voltage with frequency f4 satisfying $$f4 = (½) \times v/W$$

is applied to vibrator 11e, single node 18 of standing wave 17 is generated in an area of channel groove 7 facing vibrator 11e. At this moment, if the driving voltage is decreased, only large solid component 16b concentrates.

It is known that, if solid components 16a and 16b made of spherical and fine particles, the strength of a force receiving from standing wave 17 is proportional to the cube of the particle diameter of the particles, namely, to the volume of each particle. The area where standing wave 17 is generated and its strength may be controlled to change the density of particles concentrating to node 18 of standing wave 17 according to the sizes of solid components 16a and 16b.

Figure 13:
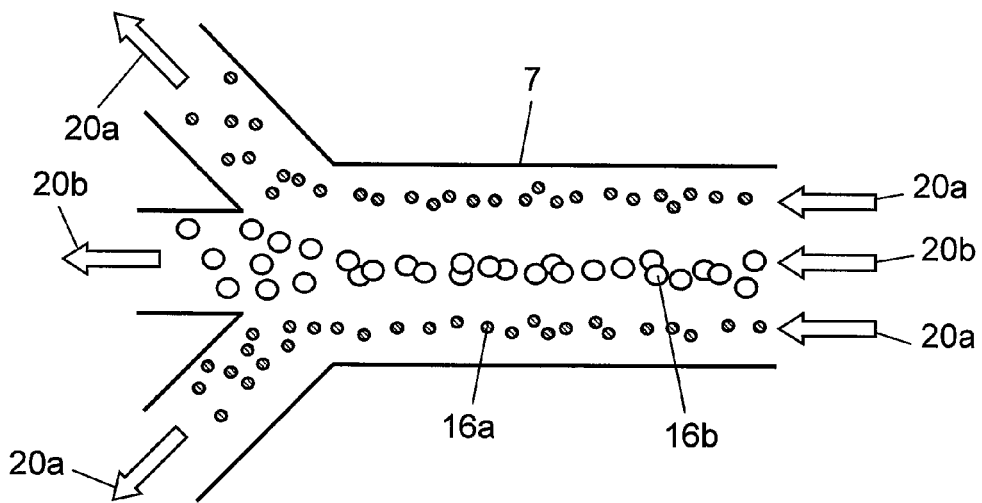
FIG. 13 is a schematic top view of the component separating device according to the invention.

Thus, the device according to this embodiment separates the mixture into flow 20a of highly-concentrating small solid component 16a and flow 20b of highly-concentrating large solid component 16b. As shown in FIG. 13, flows 20a and 20b are divided by a branch of channel groove 7 to extract small solid component 16a and large solid component 16b.

Figure 14:
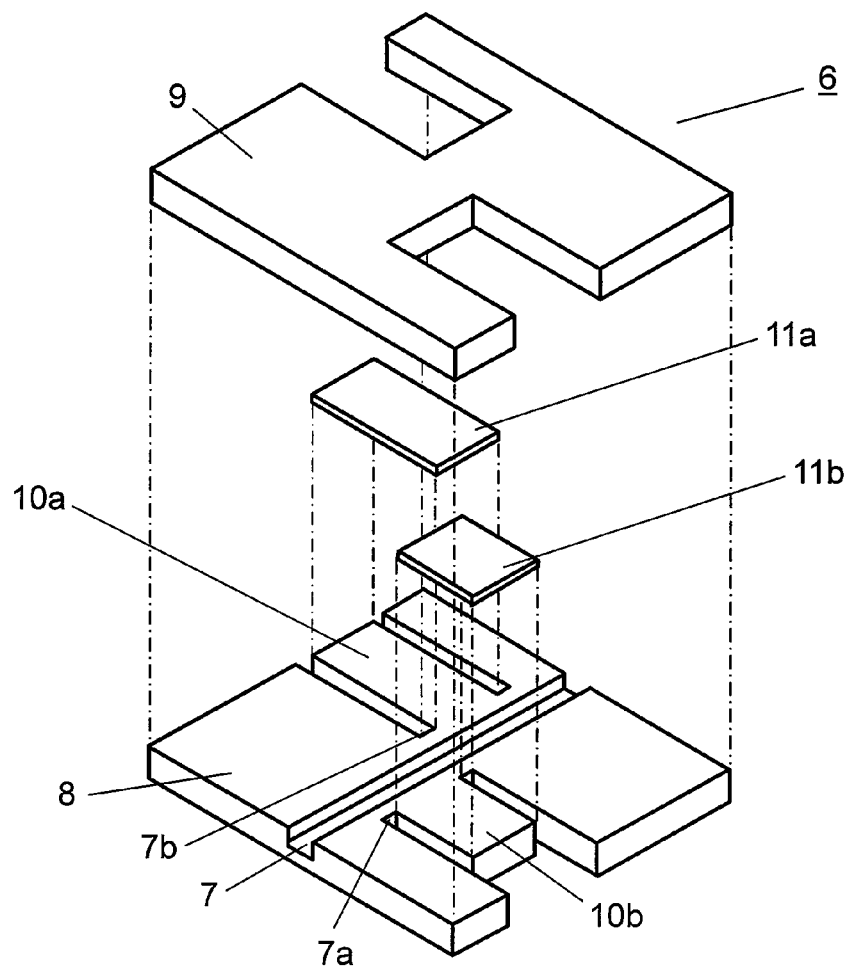
FIG. 14 is an exploded perspective view of the component separating device according to the invention.

FIG. 14 is an exploded perspective view of component separating device 6 having another shape. As shown in FIG. 14, projections 10a and 10b may be provided on outer side walls 7a and 7b at both sides of the substrate opposite to channel groove 7, respectively. In this structure, vibration sources are provided on the outer walls facing each other, and reduce interference of the respective frequencies even when projection 10a and projection 10b are driven simultaneously to each other.

Exemplary Embodiment 5

Figure 15:
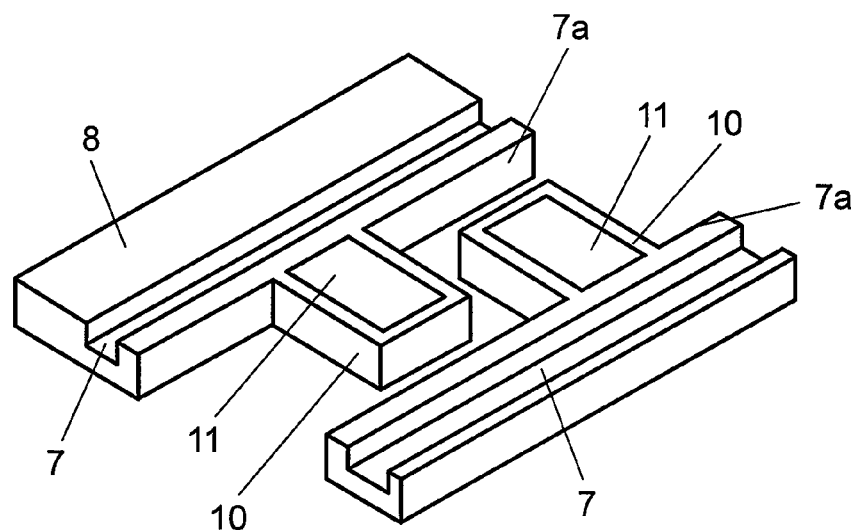
FIG. 15 is a perspective view of a substrate and a projection according to the invention.

FIG. 15 is a perspective view of substrate 8 and projection 10 according to Exemplary Embodiment 5 of the present invention. As shown in FIG. 15, the device according to this embodiment is different from the device according to Embodiment 2 in that plural channel grooves 7 are provided, and that projections 10 provided on outer side walls 7a of the substrate which are opposite to channel grooves 7 and face each other are adjacent to each other.

According to this embodiment, vibrators 11 are provided on projections 10. Even if vibrators 11 are adjacent to each other, as shown in the figure, the vibrators have spaces between them, thereby suppressing interference of respective acoustic waves. Plural vibrators 11 can be positioned close to each other, and thus the space inside the device is effectively used.

The device according to this embodiment is applicable not only to the device having plural channel grooves 7, but also to the device having channel groove 7 is curved and branched as well since portions of channel groove 7 may face each other. In these cases, projections 10 arranged on the side walls of the portions of channel groove 7 adjacent to each other can be adjacent to each other as well, thereby suppressing interference of acoustic waves in a small space.

Exemplary Embodiment 6

Figure 16:
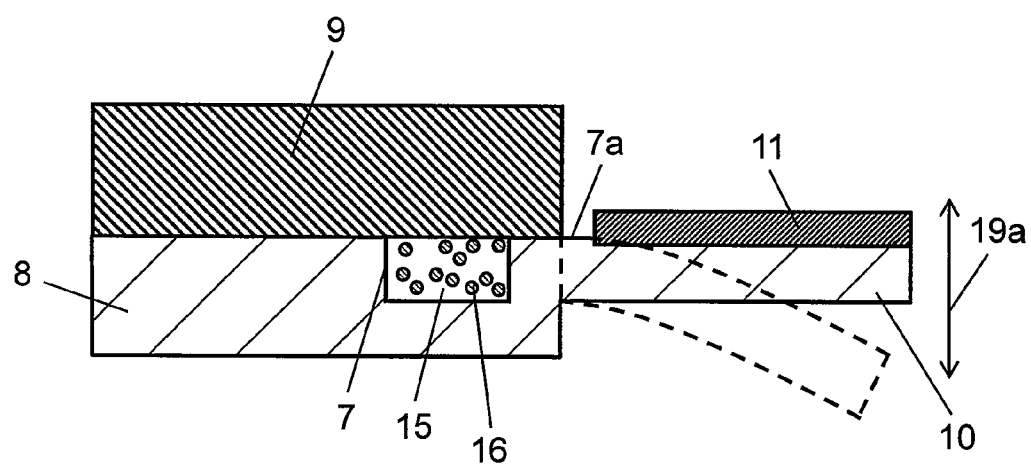
FIG. 16 is a schematic sectional view of the component separating device according to the invention for illustrating an operation of the device.

FIG. 16 is a schematic sectional view of component separating device 6 according to Exemplary Embodiment 6 of the present invention for illustrating an operation of the device. As shown in FIG. 16, the device according to this embodiment is different from the device according to Embodiment 1 in that projection 10 has a thickness smaller than that of substrate 8 and substantially identical to the depth of channel groove 7. This structure increases the displacement of warping vibration 19a and the strength of standing wave 17 generated in channel groove 7. The depth of channel groove 7 is substantially identical to the thickness of projection 10. This arrangement allows vibration to propagate intensively to channel groove 7, thereby further increasing the strength of standing wave 17 generated in channel groove 7.

Exemplary Embodiment 7

Figure 17:
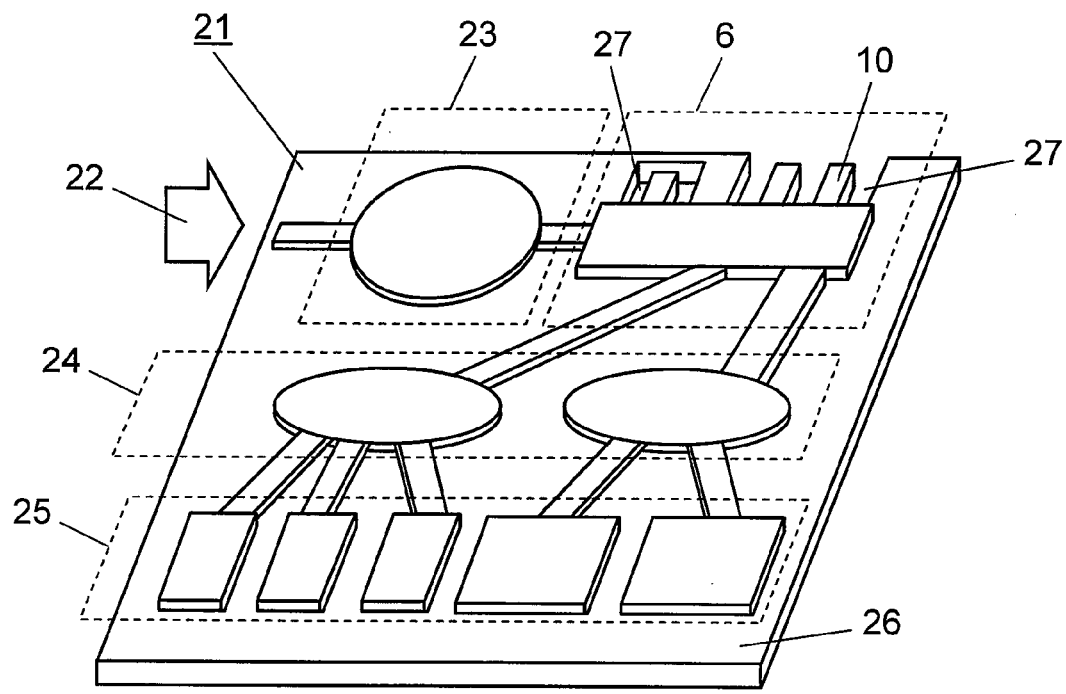
FIG. 17 is a perspective view of a chemical analysis device according to the invention.

FIG. 17 shows chemical analysis device 21 for a blood test according to this embodiment including component separating device 6 according to Embodiment 1 described above. Chemical analysis device 21 includes test substance inlet 22, transfer section (pump) 23 connected with test substance inlet 22, component separating device 6 connected with transfer section 23, reaction section 24 connected with component separating device 6, and analysis section 25 connected with reaction section 24.

Samples blood, upon being put into test substance inlet 22, is transferred to component separating device 6 through transfer section 23, and then is separated into the components of the blood through channel groove 7 (not shown). When each component reaches each reaction section 24, a reagent is put into reaction section 24 to start a chemical reaction. Then, analysis section 25 reads data on this chemical reaction. Chemical analysis device 21 according to this embodiment is made of silicon substrate 26 having a square shape having sides ranging from 20 mm to 30 mm as a base.

Chemical analysis device 21 has space 27 provided around projection 10 of component separating device 6. This space prevents vibration of the vibrator (not shown) on projection 10 from diffusing into surroundings, thereby increasing the strength of standing wave 17 generated inside channel groove 7.

Space 27 around projection 10 reduces the weight of the device.

Chemical analysis device 21 according to the embodiment may include component separating device 6 according to any one of Embodiments 2 to 6, providing the same effects. Chemical analysis device 21 particularly including component separating device 6 according to Embodiment 6 have space 27 formed above and below projection 10, thus reducing the weight of the entire device and reducing the attenuation of acoustic waves.

INDUSTRIAL APPLICABILITY

According to the present invention, components of a mixed solution, such as blood or emulsion, of liquid component and solid component can be separated into the components, and thus useful for a component separator and a component analyzer.

The invention claimed is:

1. A component separating device adapted to separate a solid component from a mixture of the solid component and a liquid component, said device comprising:
   a substrate having a channel groove provided in an upper surface of the substrate, the channel groove being adapted to introduce the mixture thereto;
   a seal provided above the substrate so as to cover an upper opening of the channel groove;
   a first projection provided on an outer side wall of the substrate opposite to the channel groove; and
   a vibrator causing the first projection to warp and vibrate in a depth direction of the channel groove,
   wherein the first projection has a resonance frequency f satisfying $$f=(n/2) \times v/W,$$

where n is a natural number, a width of the channel groove is W, and a speed of sound in the liquid component is v.

2. The component separating device of claim 1, wherein the first projection and the substrate are made of a single substrate.

3. The component separating device of claim 1, wherein the vibrator includes a first electrode, a piezoelectric body provided on the first electrode, and a second electrode provided on the piezoelectric body.

4. The component separating device of claim 1, further comprising a further vibrator causing the first projection to warp and vibrate in the depth direction of the channel groove.

5. The component separating device of claim 1, further comprising a second projection provided on the outer side wall of the substrate opposite to the channel groove.

6. The component separating device of claim 1, further comprising a second projection provided on a further outer side wall of the substrate opposite to the channel groove, the further outer side wall being opposite to the outer side wall.

7. The component separating device of claim 1, wherein the first projection has a resonance frequency f1 satisfying $$f1 = n \times v/W,$$ and the second projection has a resonance frequency f2 satisfying $$f2 = (\tfrac{1}{2}) \times v/W \text{ or } f2 = (\tfrac{1}{2} + n) \times v/W.$$

8. The component separating device of claim 1, further comprising:
- a further substrate having a further channel groove provided in an upper surface of the further substrate, the further channel groove being adapted to introduce the mixture thereto;
- a second projection provided on a further outer side wall of the further substrate opposite to the further channel groove; and
- a further vibrator causing the second projection to warp and vibrate in a depth direction of the further channel groove, wherein,
  - the channel groove and the channel groove face each other and
  - the first and second projections are adjacent to each other.

9. The component separating device of claim 1, wherein the first projection has a thickness smaller than a thickness of the substrate.

10. The component separating device of claim 4, wherein the vibrator and the further vibrator vibrate at a secondary resonance frequency with phases having different from each other by 180 degrees.

11. The component separating device of claim 5, wherein the first and second projections have shapes different from each other.

12. A chemical analysis device comprising:
- a test substance inlet;
- a transfer section connected with the test substance inlet;
- the component separating device of claim 1 connected with the transfer section;
- a reaction section connected with the component separating device; and
- an analysis section connected with the reaction section, wherein a space is provided around the projection.

13. The component separating device of claim 6, wherein the first and second projections have shapes different from each other.

* * * * *